US008317782B1

(12) United States Patent
Ellman et al.

(10) Patent No.: US 8,317,782 B1
(45) Date of Patent: Nov. 27, 2012

(54) NON-ABLATIVE RADIO-FREQUENCY TREATMENT OF SKIN TISSUE

(75) Inventors: Alan G. Ellman, Oceanside, NY (US); Jon C. Garito, Oceanside, NY (US)

(73) Assignee: Ellman International, Inc., Oceanside, NY (US)

( * ) Notice: Subject to any disclaimer, the term of this patent is extended or adjusted under 35 U.S.C. 154(b) by 852 days.

(21) Appl. No.: 11/546,850

(22) Filed: Oct. 13, 2006

(51) Int. Cl.
*A61B 18/14* (2006.01)
(52) U.S. Cl. .............................. 606/32; 606/41; 607/99
(58) Field of Classification Search ............. 606/41–45, 606/49, 32; 607/99
See application file for complete search history.

(56) References Cited

U.S. PATENT DOCUMENTS

| | | | | |
|---|---|---|---|---|
| 4,271,837 A * | 6/1981 | Schuler | | 606/39 |
| 5,916,158 A * | 6/1999 | Webster, Jr. | | 600/374 |
| 6,228,078 B1 * | 5/2001 | Eggers et al. | | 606/32 |
| 6,231,571 B1 * | 5/2001 | Ellman et al. | | 606/41 |
| 6,296,637 B1 * | 10/2001 | Thorne et al. | | 606/41 |
| 6,432,105 B1 * | 8/2002 | Ellman et al. | | 606/48 |
| 6,730,323 B1 * | 5/2004 | Murley et al. | | 424/487 |
| 6,766,202 B2 * | 7/2004 | Underwood et al. | | 607/99 |
| 2003/0158545 A1 * | 8/2003 | Hovda et al. | | 606/32 |
| 2004/0111087 A1 * | 6/2004 | Stern et al. | | 606/41 |
| 2004/0236203 A1 * | 11/2004 | Salvo | | 600/396 |
| 2006/0009757 A1 * | 1/2006 | Long | | 606/41 |
| 2007/0055226 A1 | 3/2007 | Garito et al. | | |

OTHER PUBLICATIONS

Kushikata, et al., (2005). 'Is topical anesthesia useful in noninvasive skin tightening using radiofrequency?' J. Dermatologic Surgery 2005; 31:526-533. (8 page total).
Fitzpatrick, et al. (2003). 'Multicenter study of noninvasive radiofrequency for periorbital tissue tightening'. Lasers in Surgery and Medicine 2003; 33:232-242. (12 page total).
Fritz, et al. (2004). 'Radiofrequency treatment for middle and lower face laxity'. Arch Facial Plastic Surgery 2004; 6:370-373. (4 pages total).

* cited by examiner

*Primary Examiner* — Lee S Cohen
(74) *Attorney, Agent, or Firm* — Ganz Law, P.C.

(57) ABSTRACT

A radio-frequency electrode that is specially configured to provide a reasonably uniform electric field distribution at the skin surface of a patient being treated to improve the skin appearance. Harmful burning is avoided by employing one of the following four features: pre-applying to the skin a thermal gel, a known thermally and electrically-conductive material, using low radio-frequency power at 3.8-4 MHz, relying on the natural cooling provided by a highly conductive electrode material, and continuously moving the electrode while in contact with the skin. Preferably, all four features are combined in carrying out the cosmetic procedure of the invention. In a preferred embodiment, the highly conductive electrode material is an alloy comprised mainly of silver with a small percentage of ingredients added to strengthen the silver alloy electrode and preserve its luster and the active surface of the electrode is configured as a section of a sphere, or as dome shaped.

16 Claims, 2 Drawing Sheets

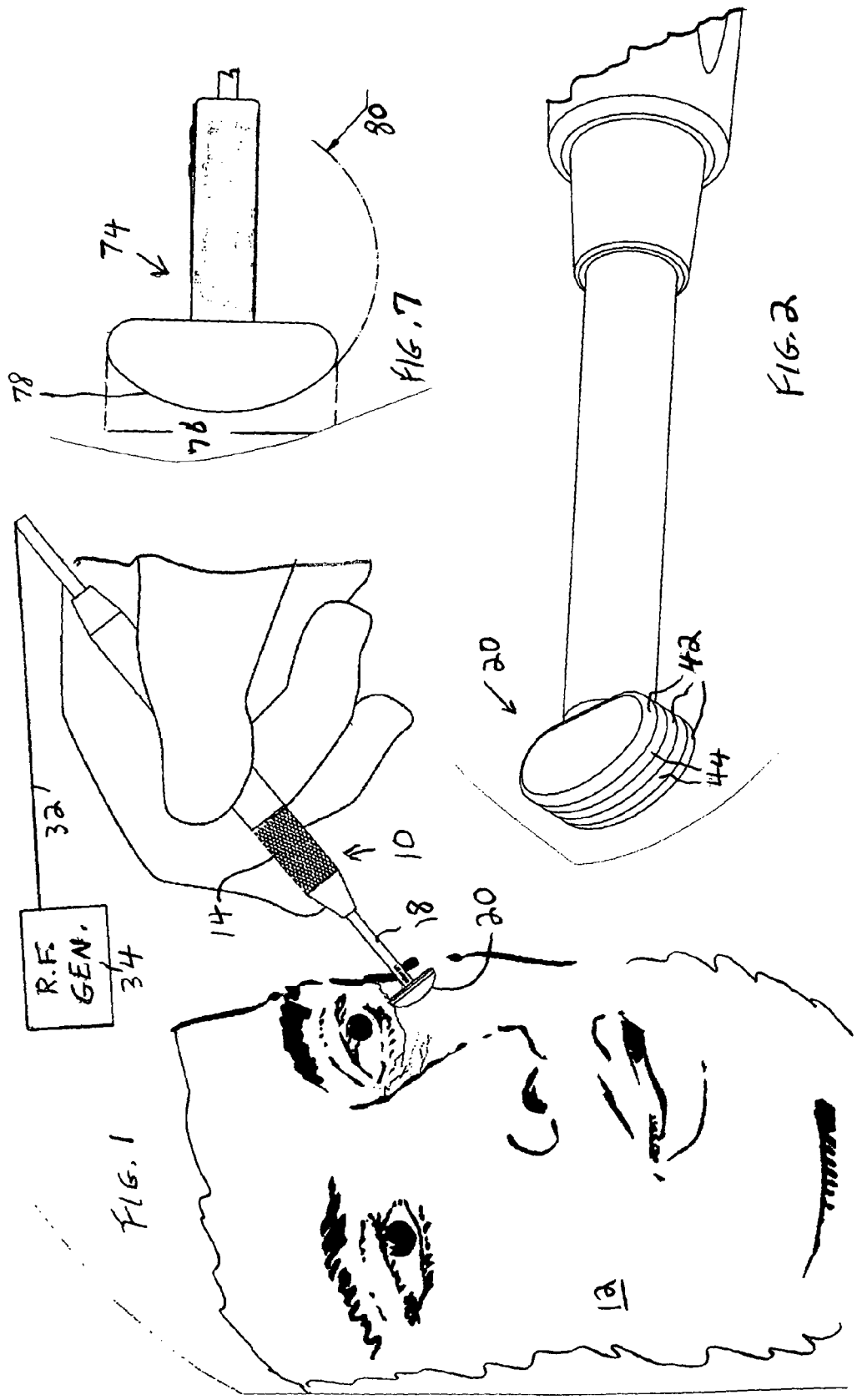

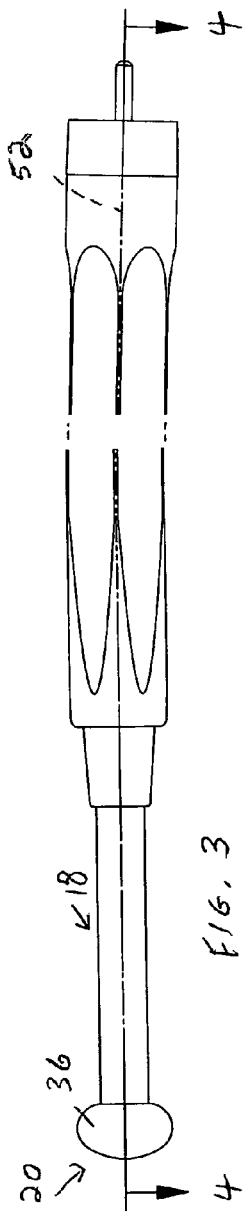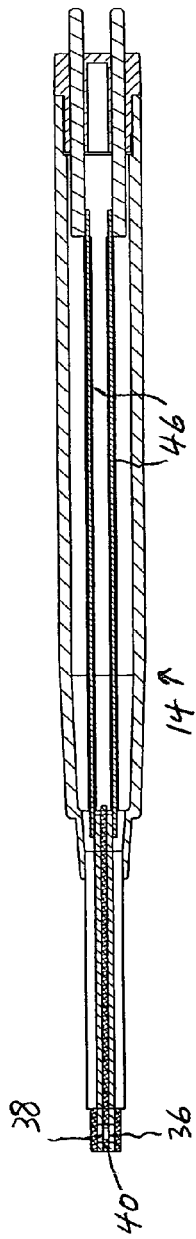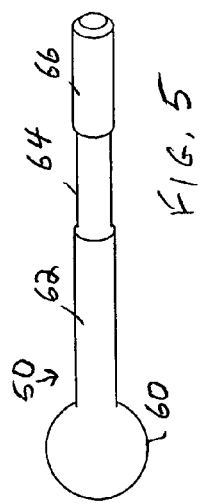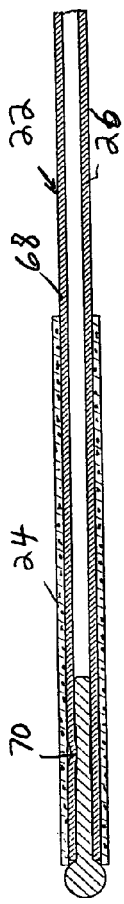
FIG. 3
FIG. 4
FIG. 5
FIG. 6

NON-ABLATIVE RADIO-FREQUENCY TREATMENT OF SKIN TISSUE

This invention relates to a procedure for treating skin tissue using non-ablative radio-frequency energy. It also relates to bipolar and monopolar electrodes for use in such procedures.

BACKGROUND OF THE INVENTION

Our prior U.S. Pat. No. 6,432,105B1 describes a novel electrosurgical instrument in particular a bipolar electrosurgical instrument that is configured for use in minimally invasive surgery (MIS) and other electrosurgical procedures. The instrument is constructed with a rigid end as a bipolar electrode comprising spaced rounded electrodes. The electrode preferably comprises spaced hemispherically-shaped electrically conductive members projecting from the end of the housing. When energized, a bipolar discharge is generated between the bare ends of the electrode. To our knowledge, such a configured electrode has not been used nor suggested for use for topical application to the skin of a patient for the non-ablative treatment of periorbital rhytides and midface laxity or in general removal of wrinkles or other cosmetic skin tightening procedures to improve the appearance of skin tissue.

Among the features described in the prior patent is the use of 3.8-4 MHz radio-frequency (RF) energy especially because of its ability to combine cutting and hemostasis during the procedure.

With the emerging trend of aesthetic medical therapy, several modalities have been developed to further the drive for human self-preservation. Cosmetic and oculoplastic surgery have increasingly crossed paths in the pursuit of noninvasive procedures with which to rejuvenate the facial skin. One of the recent innovations in oculofacial surgery involves the use of nonablative laser and light sources to reduce the appearance of facial creases. However, disadvantages of laser-based treatments include the necessity for multiple treatments and results that may regress or have unpredictable results. Moreover, the efficacy of such systems done on cases with severe skin laxity does not appear satisfactory in some patients.

Recent advances in management of flaccid skin disorders have led to the development of radiofrequency treatment. Several devices were developed to deliver radiofrequency energy in a non-ablative fashion. The principle of radio-frequency differs from laser-based methods in that it produces an electric current that generates heat through resistance in the dermis and subcutaneous tissue rather than a selective photothermolysis employed in lasers. Studies by Kushikata et al. "Is topical anesthesia useful in noninvasive skin tightening using radiofrequency?." J. Dermatologic Surgery 2005; 31: 526-533; and Fitzpatrick R. et al. "Multicenter study of non-invasive radiofrequency for periorbital tissue tightening". Lasers in Surgery and Medicine 2003; 33:232-242; and Fritz M. et al. "Radiofrequency treatment for middle and lower face laxity." Arch Facial Plastic Surgery 2004; 6:370-373 have been initiated for the use of radiofrequency energy to improve facial rhytides and skin laxity. Some studies have involved the use of the ThermacoolTC System (Thermage, Inc). However, there was a small incidence of burns and residual scarring noted during some of the trials. In the ThermacoolTC System studies, results were deemed moderate with generally good satisfaction rates.

A disadvantage of the ThermacoolTC System is its high cost due to the use of complex electrodes, very high RF frequencies in the 6 MHz range, and the need for continuous impingement on the skin tissue being treated of an external cooling medium, such as spraying a freezing solution on the skin during application of the 6 MHz energy to avoid burns and possible patient harm.

SUMMARY OF THE INVENTION

An object of the present invention is to employ radio-frequency energy for skin conditioning but with non-ablative electrodes specially configured to increase the temperature of surface skin to reduce skin conditions that impair the beauty of natural healthy skin and without requiring external cooling or producing skin damage, such as by burning.

In accordance with a feature of the invention an electrode is used that is specially configured to provide a reasonably uniform electric field distribution at the skin surface being treated. Harmful burning is avoided by employing one of the following four features: pre-applying to the skin a thermal gel, a known thermally and electrically-conductive material, using low radio-frequency power, relying on the natural cooling provided by a highly conductive electrode material, and continuously moving the electrode while in contact with the skin. Preferably, all four features are combined in carrying out the cosmetic procedure of the invention.

In a preferred embodiment, the highly conductive electrode material is an alloy comprised mainly of silver with a small percentage of ingredients added to strengthen the silver alloy electrode and preserve its luster.

In another preferred embodiment, the active surface of the electrode is configured as a section of a sphere, or as dome shaped. It is believed that this electrode configuration contributes to the desired uniform field distribution.

It is also preferred that not only is the power setting of the radio-frequency-generating instrument set low, but also the cut/coag mode is selected. In the cut/coag mode, the radio-frequency waveform at a preferred frequency in the 3.8-4 MHz range is fully rectified before being supplied to the electrode.

The electrode of the invention can be of the monopolar or bipolar type. The referenced '105 patent illustrates in FIGS. 1-3 examples of a bipolar electrode that can be used in carrying out the invention. The monopolar version will omit the electrically-insulated layer separating the two halves of the ball end.

It is believed that radiofrequency technology produces an electric current that generates heat through resistance in the dermis and subcutaneous tissue. The thermal effect depends on the conductivity features of the treated tissue. Collagen fibrils, when heated, will denature and contract, which is believed to lead to the observed tissue tightening. Non-ablative RF treatment has a lower risk of complications, shorter recovery time and less disruption of regular activities.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals designating the same or similar elements.

BRIEF DESCRIPTION OF THE DRAWINGS

In the drawings:

FIG. 1 is a schematic view of one form of a bipolar electrode according to the invention mounted in a handle or handpiece and shown being applied by a surgeon to the face of a patient;

FIG. 2 is a perspective view of another form of bipolar electrode according to the invention;

FIGS. 3 and 4 are a top and a cross-sectional view along the line 4-4, respectively, of a bipolar electrode in accordance with the invention mounted in a typical handpiece;

FIGS. 5 and 6 are a perspective view, and a cross-sectional view, respectively, of one form of a monopolar electrode according to the invention within a supporting tube;

FIG. 7 is a side view of one form of dome-shaped monopolar electrode for use in accordance with the invention.

DETAILED DESCRIPTION OF PREFERRED EMBODIMENTS

In the present application, FIG. 1 is a schematic view of one form of radio-frequency generating instrument 10 in accordance with the invention shown being applied to the face 12 of a patient. It comprises a handle or handpiece 14 with a conventional front end adapted to receive and hold rigidly the shank end (not shown in FIG. 1) of an elongated electrode 18 whose working end 20 is shown at the left. The handle or handpiece 14 is electrically-insulating or if conductive is covered with an electrically-insulating coating. Similarly, the electrode's elongated shaft 22 (the FIG. 2 embodiment is bipolar but the FIG. 6 embodiment is monopolar and has a similar external construction) is partly coated with an electrically-insulating coating 24, leaving bare the shank end 26 for electrically-conductive engagement with the handle or handpiece and the active electrode(s) at the working end 20. The electrode 18 is long enough to be applied by the surgeon so as to readily contact any surface region of exposed skin of the patient's head or neck, typically the sites where skin treatments are desired. At the right end of the handle 14 is a cable 32 which contains two insulated wires for receiving bipolar radio-frequency currents from a conventional radio-frequency apparatus 34.

The bipolar electrode of FIG. 1 may have spherical front formed by two thin hemispherical sides 36, 38 separated by an insulating region 40, as depicted in FIGS. 3 and 4, and as illustrated in the '105 patent at FIGS. 1-3, or may have multiple electrically-conductive sections 42 separated by electrically-insulated sections 44, as depicted in FIG. 2, forming a more dome-shaped front face similar to FIG. 5 of the '105 patent. As illustrated in FIG. 4, with two bipolar sections, separate feed wires 46 in the handle or handpiece 14 supply bipolar radio-frequency currents to the hemispherical sides 36, 38. Where more than two electrically-conductive sections are present, as in FIG. 2 where three sections 42 are shown separated by electrically-insulated sections 44, then to the adjacent electrically-conductive sections would be supplied alternate poles of the bipolar voltages. In both cases, the radio-frequency currents are constrained to and flow between adjacent electrically-conductive sections at the front of the working end 20. In the cross-section of FIG. 4, which is taken along the minor diameter of the dome, the two electrically-conductive sections 36, 38 are separated by the electrically-insulated layer 40, and in this particular embodiment, the shape of the working end (FIG. 3) is more elliptically shaped with its long dimension longer than its transverse dimension, the flat sides of the working end also being coated with electrically-insulated material (not shown).

For purposes of the invention, when a bipolar electrode is employed, the thin multiple electrically-conductive sections of the FIG. 2 embodiment are preferred. When the electrically-conductive sections 42 are thin, then the bipolar discharges across the electrically-insulated sections 44 are very close to one another which increases the uniformity of the heating.

In this description, by "axial" is meant parallel to the long axis 52 of the electrode (horizontal in FIGS. 3, 4 and 6). By "lateral" is meant transverse to the long axis 52 of the electrode. "Lateral" is intended to include 90° as well as 45° as in the embodiments of FIGS. 6-9 of the '105 patent. In other words, the working end 20 of the electrode need not be in alignment with its shaft, but can extend at oblique and even acute angles with respect to the shaft. The two insulated wires 46 terminate at the left end of the handle 14 in a connector having prongs which can be plugged into a standard bipolar socket or cable which connects the assembly to the radio-frequency apparatus 34.

Once the surgeon has positioned the working end 20 of the instrument with respect to the tissue to be operated on, he or she then activates the radio-frequency apparatus 34 causing a discharge of RF bipolar currents between the bare electrodes 36, 38 capable of causing heating of tissue as will be described in more detail below. Other usable mechanical or electrical structures following the teachings of the prior patent will be appreciated by those skilled in this art. As with the embodiments of the prior application, the insulating tube coating on the shaft 18 will prevent accidental touching of patient tissue by the electrode sides, so that the bipolar discharge is localized to the spacing between the bare ends 36, 38. The surgeon positions the electrodes 36, 38 so as to touch or press lightly on the tissue to be treated as needed for the procedure being followed.

Among the electrodes depicted for the non-ablative procedure, the dome-shaped electrode 74 depicted in FIG. 7 is among the preferred electrodes. In the embodiment illustrated, the diameter 76 across the dome is preferably from about 5-25 mm large, the larger sizes being preferred. The actual shape of the front surface 78 is a segment of a sphere whose radius indicated by 80 is about 20-40% larger than the dome diameter 76. For example, for a dome diameter of 20 mm, the sphere radius is about 26 mm. The advantage of the monopolar dome shape is that the dome shaped electrode combines the advantages of spherical, and flat electrodes, and also is more efficient in terms of RF energy use. The advantage of the larger spherical front is that the active front surface has a smoother curvature, and hence the monopolar RF energy is more uniform over the whole surface area. This is valuable in terms of effect and safety for a non-ablative skin tightening method. Reduced uniformity of the RF energy over the surface area may cause charges to concentrate in specific regions of the electrodes, and could cause an unintentional burn to the patient. The curvature and increased uniformity of the dome shaped electrode leads to more uniform RF energy over the whole surface area and hence is safer for the non-ablative skin tightening method.

As explained below, the preferred metal for the working end of the electrode is a highly electrically-conductive and thermally conductive material, a silver alloy being preferred. For cost reasons, the silver alloy shank is supported in a tube of a suitable electrically-conductive metal such as brass or stainless steel, brass being preferred because it has a higher thermal conductivity. A suitable thickness of the insulator 34 is about 0.02-0.04 inches. The diameter of the hemispherical assembly can vary between about 2-5 mm. Preferably, the radius of curvature of each of the quarter-spherical electrode is about 2-25 mm. The shaft outside diameter is typically about 5-10 mm.

Another electrode embodiment 50 of the invention is depicted in FIGS. 5 and 6, in which the working end is ball shaped. Typical ball diameters are from about 2-26 mm. The electrode is monopolar. Preferably, the electrode comprises a silver alloy portion, depicted in FIG. 5, comprising the ball end 60, a distal shank portion 62, a recessed shank portion 64, and a proximate shank portion 66. For cost reasons, the latter distal, recessed, and proximate shank portions are supported in an electrically-conductive tube 68 which is then crimped or mechanically swaged 70 in over the recessed portion 64 to lock the silver alloy portion to and inside of the electrically-conductive tube, for example of brass. The exterior is then partially coated with an electrically-insulated coating 24 to leave exposed an electrically-conductive tubular shank 26 which is mounted in the front end of the handpiece. The ball shape can be a regular sphere, or the front face of a segment of a sphere with several radii. The spherical or pseudo-spherical front tends to increase the uniformity of the electric field at the skin surface.

A feature of the invention is to use the electrode of the invention in a non-ablative cosmetic procedure under certain preferred conditions, as explained below, to heat the underlying subcutaneous tissue to a temperature sufficient to reduce skin defects by firming and smoothing the skin but without causing permanent damage to the skin.

Studies were carried out to test the efficacy of the procedure of the invention.

In one series of studies, patients were treated with an Ellman Radio-Frequency Generating Instrument (Dual-Frequency IEC unit). 17 patients were treated: in 11 of them the treatment was performed after either superior or inferior blepharoplasty; the remaining 6 had serious periocular wrinkles but no previous blepharoplasty. The same surgeon performed the operation with the same radio-frequency instrument without anesthesia. A monopolar electrode as illustrated in FIG. 5 was used, supplied by Ellman, which was indicated to be a silver alloy. The active electrode end had a curved surface that could be described as dome-shaped or ball-shaped having a diameter of about 5 mm. The electrode when activated was moved continuously in circular movements up and down the skin surface area being treated. A very low power was used with the instrument outputting about 3-5 watts. While the patients reported discomfort during the treatments, pictures of the patients taken before treatment, and 30 and 60 days after treatment, showed improvement of the eye region, reducing all wrinkles with minimal post-op discomfort and inconvenience.

In another study, the Ellman Surgitron Radiofrequency IEC unit was used on patients with periorbital rhytides and midface laxity. Pre- and post-application photographs were taken.

7 females and 1 male with ages ranging from 29-63 years old with Fitzpatrick skin wrinkle classification I-III presenting with upper and lower lid rhytides, skin laxity of the eyelids, and midface area were enrolled into this case-control study. A conventional thermal reduction microclysmic gel was applied to the periorbital and midface regions after effective removal of make-up or other facial emulsions. Neither topical anesthesia nor sedative was given pre-operatively. The curved frontal surface of a 1 cm diameter sphere shaped ball electrode of a silver alloy composition alloy was lightly moved in a circular motion covering the entire area of the periorbital, frontal and midface area. The upper eyelids of all patients were not subjected to treatment. The Surgitron IEC instrument was adjusted to the coagulation and cutting mode producing continuously rectified current waveforms with an electrical output range of 12-25 J/cm2 (average of 18.5 J/cm2) roughly equivalent to about 15-30 watts of power, which is low power. The electrical current was typically increased to the patients' maximal level of tolerance. During the procedure, the electrode was moved over the tissue in a spiral movement over an area of approximately 1 cm diameter. Tolerance was noted to be maximal with evidence of erythema at the site of electrode application along with pain. 5 weekly radiofrequency sessions were done for each patient with the radiofrequency probe passing over the above-mentioned areas 3-4 times.

3 objective observers noted significant differences between the pre-radiofrequency treatment and post-radiofrequency treatment photographs, specifically, a reduction in periorbital and midface rhytides in the patients. The most commonly noted adverse reaction was transient erythema lasting for a few hours to a day, tolerable pain during the procedure described as a warm sensation and mild edema lasting for one to two days. There were no scarring, burns, bruising nor dysesthesia noted in any of the subjects following the treatment.

The radio-frequency apparatus used outputted high frequency (RF) radio-frequency currents in the range of about 3.8-4.0 MHz. What characterized both surgical tests was the use of 3.8-4.0 MHz radio-frequency currents at low powers with an electrode that had an active surface that was spherical or dome-shaped, and with the surface being maintained below a harmful temperature to avoid burning through the use of a highly thermally-conductive silver alloy and a thermal electrically-conductive gel. The silver alloy electrode was solid metal constituted mainly of silver with a small amount of germanium and indium to increase its hardness and resistance to corrosion. The compositions described in our copending application Ser. No. 11/180,809, filed Jul. 14, 2006, the contents of which are herein incorporated by reference, are deemed suitable for this application with the solid electrode rather than the laminated coated electrode being preferred. In general, the silver alloy preferably has a content by weight of about 93-98% by weight silver with about 1.5-4% by weight of germanium and 1-2% by weight of indium. A preferred composition is 97% silver with 2% germanium and 1% indium.

A wide variety of conductive topical gels, which are also referred to as thermal gels, can be used. Such gels are often used to reduce the contact resistance of the electrodes used in EKG scans. A myoepithelial gel commercially known as Humatrix, can be used, as well as so-called microclysmic gels. Humatrix was developed as a therapeutic wound gel to enhance healing of the wound and reduce swelling and increase elasticity of the skin. Humatrix, which is described in detail in U.S. Pat. No. 6,730,323, the contents of which are herein incorporated by reference, is a bacteriostatic protectant but with no bacteriocidal activity. The gel consist essentially of by weight percent, about 88-97% water, about 0.4-0.6% carbomer, about 1.2-7.8% propylene glycol, about 0.6-1.3% glycerin, about 0.5% DMDM Hydantoin, about 0-0.8% citric acid, about 0.1% chondroitin sulfate and animal protein, and about 0-0.6% triethanolamine. The gel is formed in three phases which are combined together, the first phase consisting essentially of about 88-99% of the water of the gel, the carbomer, the propylene glycol, and the glycerin; the second phase consisting essentially of the remaining water, the DMDM Hydantoin, and the citric acid if needed; and the third phase consisting essentially of the chondroitin sulfate and animal protein and the triethanolamine, if needed. The gel, as well as many others like it, are electrically-conductive and also thermally conductive and contribute to what we believe is an important attribute of our invention, namely, the creation of a uniform electrosurgical field at the skin surface being treated. The creation of a uniform electrosurgical field at the skin surface being treated, together with the highly conductive silver alloy electrode, the presence of the thermal gel, the use of low power electrosurgical currents at 3.8-4 MHz, and the constant movement of the electrode during the procedure are we believe mainly responsible for the skin improvements noted without permanent skin damage.

Examples of suitable radio-frequency generating apparatus are the Model SURGITRON Dual-Frequency and IEC radio-frequency units manufactured by and available from Ellman International, Inc. of Oceanside, N.Y.

In summary, radiofrequency skin tightening is a new and very promising tool for the non-surgical tightening of loose or sagging skin. Most patients will see at least a mild improvement, with minimal downtime and minimal risk. The 3.8-4 MHz radio-frequency unit that was used appears well suited for non-ablative in-office rejuvenation of the skin and provides a measurable improvement in the majority of patients treated. This procedure is believed to be an effective, non-invasive, economical and safe tool. In addition, costs connected to this new method are rather low, and even less skilled professionals can be easily trained on this technology, thanks to the low risks that its use involves.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A non-ablative procedure for reducing skin rhytides for improving the appearance of skin tissue of a patient, comprising:
   A. providing a radio-frequency handpiece comprising:
      (a) a radio-frequency electrode comprising an elongated first member having a first end and a distal second end being the active end of the electrode,
      (b) at least one electrically-conductive wire at the first end and extending through the first member for connecting to and applying to the second active end a radio-frequency voltage capable of generating radio-frequency currents,
      (c) the second end being bare and configured to form a segment of a sphere or a dome shape wherein the second end comprises an active electrode portion having a convexly curving front surface for applying RF energy to tissue and an opposing rear-facing surface that extends transversely from the shaft's longitudinal axis, the shaft's diameter or width being concentrically disposed within the diameter of the rear-facing surface, thereby defining a dome-shaped working portion disposed on the distal end of the shaft, the active electrode portion comprising a single structural unit;
   B. providing a radio-frequency generating instrument for supplying radio-frequency currents in the megacycle range to the electrically-conductive wire when activated;
   C. applying the active end of the electrode to contact the outer surface of the patient's skin tissue having the rhytides and, while activating the radio-frequency generating instrument to apply radio-frequency currents to the patient's skin tissue having rhytides, continuously moving the electrode around the skin surface to avoid damaging the contacted skin surface while heating the dermis underneath until skin rhytides on the outer skin are reduced thereby reducing the skin rhytides without ablation of the skin tissue and without requiring external cooling.

2. A procedure as claimed in claim 1, wherein the radio-frequency voltage is at a frequency of about 3.8-4 MHz.

3. A procedure as claimed in claim 2, wherein the radio-frequency currents are continuously rectified.

4. A procedure as claimed in claim 1, wherein the active end of the electrode is configured as a bipolar electrode with two half-dome-shaped electrically-conductive regions separated by an electrically-insulated region.

5. A procedure as claimed in claim 1, wherein the electrode has a dome-shape that has a front curvature that is about 20-40% larger than the diameter across the dome.

6. An electrosurgical instrument, comprising:
   a proximal handpiece having an electrically insulating surface and configured to couple with an RF generator;
   an electrode comprising a single shaft portion extending from a distal end portion of the handpiece and an active electrode portion disposed entirely on the distal end portion of the single shaft portion and configured to deliver the RF energy to target tissue;
   the active electrode portion having a convexly curving front surface for applying RF energy to tissue and an opposing rear-facing surface that extends transversely from the shaft's longitudinal axis, the shaft's diameter or width being concentrically disposed within the diameter of the rear-facing surface, thereby defining a dome-shaped active electrode portion disposed on the distal end of the shaft; and
   wherein the diameter or width of the rear-facing surface of the active electrode portion of the electrode is at least two times the outside diameter or width of the shaft portion.

7. The instrument of claim 6 wherein the diameter of the rear-facing surface is at least about 20 mm.

8. The instrument of claim 7 wherein the shape of the front surface of the dome comprises a segment of a sphere whose radius is about 20-40% larger than the rear-facing surface.

9. The instrument of claim 6 wherein the shaft portion has an electrically insulated portion extending from the distal portion of the handpiece and an electrically conductive portion disposed within the handpiece that is part of an assembly configured for electrical communication with an RF generator.

10. The instrument of claim 6 wherein the active electrode portion of the electrode is configured to deliver to contacting tissue a non-ablative energy when electrically connected to an RF generator having frequency settings comprising 3.8 to 4.0 Mhz.

11. The instrument of claim 6 wherein the electrode is configured in the instrument as a monopolar electrode.

12. The instrument of claim 6 wherein the electrode is configured in the instrument as a bipolar electrode.

13. The instrument of claim 6 wherein the rear facing surface is generally perpendicular to the shaft portion so as to provide the active electrode portion with a generally hemispherical shape.

14. An electrosurgical instrument, comprising:
   a proximal handpiece having an electrically insulating surface and configured to couple with an RF generator;
   an electrode comprising a shaft portion extending from a distal end portion of the handpiece and an active electrode portion disposed on the distal end portion of the shaft portion and configured to deliver the RF energy to target tissue;
   the active electrode portion comprising a single structural unit having a convexly curving front surface for applying RF energy to tissue and an opposing rear-facing surface that extends transversely from the shaft's longitudinal axis, the shaft's diameter or width being concentrically disposed within the diameter of the rear-facing surface, thereby defining a dome-shaped active electrode portion disposed on the distal end of the shaft; and wherein the diameter or width of the rear-facing surface of the active electrode portion of the electrode is at least two times the outside diameter or width of the shaft portion.

15. The instrument of claim 14 wherein the active electrode portion is disposed entirely on a single shaft portion.

16. The instrument of claim 14 wherein the rear facing surface is generally perpendicular to the shaft portion so as to provide the active electrode portion with a generally hemispherical shape.

* * * * *